United States Patent [19]
Brandes et al.

[11] Patent Number: 5,240,952
[45] Date of Patent: Aug. 31, 1993

[54] FUNGICIDAL AGENTS

[75] Inventors: Wilhelm Brandes, Leichlingen; Gerd Hänssler, Leverkusen; Paul Reinecke, Leverkusen; Hans Scheinpflug, Leverkusen; Graham Holmwood, Wuppertal, all of Fed. Rep. of Germany

[73] Assignee: Bayer Aktiengesellschaft, Leverkusen, Fed. Rep. of Germany

[21] Appl. No.: 885,417

[22] Filed: May 19, 1992

Related U.S. Application Data

[60] Division of Ser. No. 762,274, Sep. 19, 1991, Pat. No. 5,137,903, which is a division of Ser. No. 711,671, Jun. 6, 1991, Pat. No. 5,147,887, which is a division of Ser. No. 587,193, Sep. 24, 1990, Pat. No. 5,082,855, which is a division of Ser. No. 487,680, Mar. 2, 1990, Pat. No. 4,990,527, which is a division of Ser. No. 330,331, Mar. 29, 1989, Pat. No. 4,933,337, which is a division of Ser. No. 193,437, May 12, 1988, Pat. No. 4,845,111, which is a continuation of Ser. No. 89,698, Aug. 20, 1987, abandoned, which is a division of Ser. No. 810,549, Nov. 25, 1985, abandoned, which is a continuation of Ser. No. 646,591, Aug. 31, 1984, abandoned.

[30] Foreign Application Priority Data

Sep. 16, 1983 [DE] Fed. Rep. of Germany ....... 3333411

[51] Int. Cl.⁵ .................... A01N 43/50; A01N 43/64; A01N 43/76
[52] U.S. Cl. .................... 514/376; 514/383; 514/391
[58] Field of Search ................... 514/383, 376, 391

[56] References Cited

U.S. PATENT DOCUMENTS 4,584,309  4/1986  Ishiguri et al. ............. 514/383

FOREIGN PATENT DOCUMENTS 0052424  5/1982  European Pat. Off.
1037620  9/1991  United Kingdom ............. 514/394

Primary Examiner—Allen J. Robinson
Attorney, Agent, or Firm—Sprung Horn Kramer & Woods

[57] ABSTRACT

A fungicidal composition comprising a fungicidally effective amount of (i) a substituted 1-hydroxyethyl-triazole of the formula

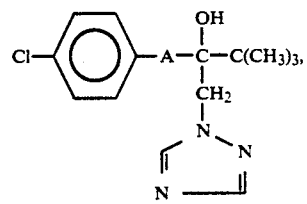

in which
A is —CH$_2$CH$_2$— or —CH=CH—, or an addition product thereof with an acid or metal salt, and (ii) at least one member selected from the group consisting of
A) wettable sulphur,
B) a polyhalogenoalkylthio derivative,
C) a guanidine derivative,
D) an aromatic carboxylic acid derivative,
E) a dithocarbamate,
F) a benzimidazole derivative,
G) an imidazole or triazole derivative,
H) a phosphoric acid ester,
I) a tetrahydroquinoline derivative,
J) an S,N-heterocyclene compound,
K) a urea derivative,
L) a sulphonamide derivative,
M) a polyhydroxy ether derivative,
N) a triazine derivative,
O) a copper complex salt,
P) an N-formyl derivative,
Q) a morpholine derivative,
R) a quinoxaline derivative, and
S) a dicarboximide derivative.

2 Claims, No Drawings

FUNGICIDAL AGENTS

This is a division of application Ser. No. 07/762,279, filed Sep. 19, 1991 now U.S. Pat. No. 5,137,908, which is a division of application Ser. No. 711,671, filed Jun. 6, 1991 now U.S. Pat. No. 5,147,887, which is a division of Ser. No. 587,193, filed Sep. 24, 1990, now U.S. Pat. No. 5,082,855, which is a division of Ser. No. 487,680, filed Mar. 2, 1990, now U.S. Pat. No. 4,990,527, which is a division of application Ser. No. 330,331, filed Mar. 29, 1989, now U.S. Pat. No. 4,933,337, which is a division of application Ser. No. 193,437, filed May 12, 1988, now U.S. Pat. No. 4,845,111, which is a continuation of application Ser. No. 089,698, filed Aug. 26, 1987, now abandoned, which is a division of application Ser. No. 801,549, filed Nov. 25, 1985, now abandoned, which is a continuation of application Ser. No. 646,591, filed Aug. 31, 1984, now abandoned.

The present invention relates to new fungicidal active compound combinations of particular known substituted 1-hydroxyethyl-triazolyl derivatives and other known fungicidal active compounds.

It is already generally known that mixtures containing 1,2,4-triazole derivatives, such as, for example, 1-(4-chlorophenoxy)-3,3-dimethyl-1-(1,2,4-triazol-1-yl)-2-butanone, in combination with other known fungicides have a considerably more powerful action than the individual components. See U.S. Pat. No. 4,251,512 issued Feb. 17, 1981.

However, the effectiveness of these active compound mixtures is not competely satisfactory in all fields of use.

It has been found that new active compound combinations of particular substituted 1-hydroxyethyl-triazolyl derivatives of the formula (I)

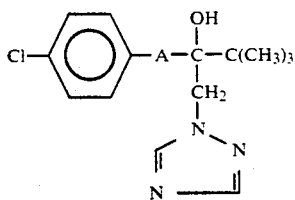

in which
A represents the grouping —CH$_2$CH$_2$— or —CH=CH— and acid addition salts and metal salt complexes thereof, and
(A) Wettable sulphur and/or
(B) Polyhalogenoalkylthio derivatives of the formulae

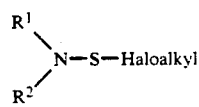

(IIa) $R^1 = (CH_3)_2N$—$SO_2$—,

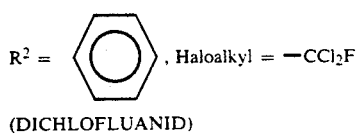, Haloalkyl = —CCl$_2$F (DICHLOFLUANID)

-continued (IIb) $R^1$ and $R^2$ = 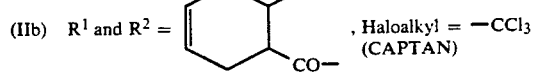, Haloalkyl = —CCl$_3$
(CAPTAN)

(IIc) $R^1$ and $R^2$ = 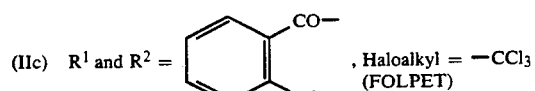, Haloalkyl = —CCl$_3$
(FOLPET)

(IId) $R^1$ and $R^2$ = 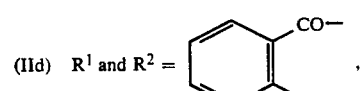,

Haloalkyl = —CCl$_2$—CHCl$_2$
(CAPTAFOL)

and/or
(C) a guanidine derivative of the formula $$\text{n-C}_{12}\text{H}_{25}-\text{NH}-\overset{\overset{\displaystyle NH}{\|}}{C}-\text{NH}_2 \quad \times \quad \text{CH}_3-\text{COOH} \quad \text{(III)}$$
(DODINE)

and/or
(D) An aromatic carboxylic acid derivative of the formula

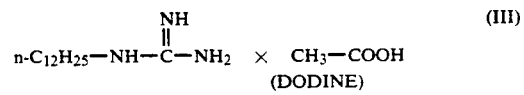

(TETRACHLOROPHTHALIDE)

and/or
(E) Dithiocarbamates of the formulae

(Va)  $R^1 = H$, $M = Zn$
(ZINEB)

(Vb)  $R^1 = H$, $M = Mn$
(MANEB)

(Vc)  Mixture of (Va) and (Vb)
(MANCOZEB)

(Vd)  $R^1 = CH_3$, $M = Zn$
(PROPINEB)

and/or
(F) Benzimidazole derivatives of the formulae

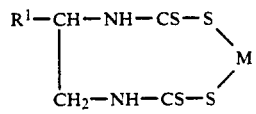

(VIa)

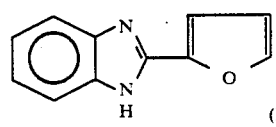

(FUBERIDAZOL)

-continued (VIb)

[Structure: benzimidazole with NH-COOCH₃]
(CARBENDAZIM)

and/or
(G) Derivatives of imidazoles and triazoles, of the formulae

[Structure: X-phenyl-O-CH-A-C(CH₃)₃ with triazole]

(VIIa) X = Cl, A = CO
(TRIADIMEFON)

(VIIb) X = Cl, A = CH(OH)
(TRIADIMENOL)

(VIIc) X = phenyl, A = CH(OH)
(BITERTANOL)

(VIId)
[Structure: 2,4-dichlorophenyl-CH(O-CH₂-CH=CH₂)-CH₂-N-imidazole × HNO₃]
(FUMGAFLOR)

(VIIe)
[Structure with imidazole-CO-N(C₃H₇-n)-CH₂CH₂-O-2,4,6-trichlorophenyl]
(PROCHLORAZ)

[Structure: R¹-phenyl(R²)-A-C(OH)(CH₂-triazole)-C(CH₃)(CH₂X)(CH₂Y)]

(VIIf): R¹ = Cl; R² = H; A = —CH₂CH₂—; X = F; Y = H (VIIg): R¹ = Cl; R² = H; A = —CH₂CH₂—; X = F; Y = F (VIIh): R¹ = Cl; R² = CH₃; A = —OCH₂—; X = H; Y = H (VIIi): R¹ = Cl; R² = CH₃; A = —OCH₂—; X = F; Y = H (VIIj): R¹ = phenyl; R² = H;

A = —OCH₂—; X = H; Y = H (VIIk): R¹ = Cl; R² = Cl; A = —OCH₂—; X = F; Y = H

-continued (VIII): R¹ = CH₃ON=CH—; R² = H;

A = —OCH₂—; X = H; Y = H (H) A phosphoric acid ester of the formula (VIII)

[Structure: C₂H₅O-P(=O)(S-phenyl)(S-phenyl)]
(EDIFENPHOS)

and/or
(I) A tetrahydroquinoline derivative of the formulae

[Structure: Hal-substituted tetrahydroquinoline with O-CH₂-C(=O)]

(IXa) Hal = Br
(IXb) Hal = Cl (IXc)
[Structure: fused tricyclic tetrahydroquinolinone]
(LILOLIDONE)

and/or
(J) S,N-Heterocyclene compounds of the formulae (Xa)
[Structure: methylphenyl fused thiazole-triazole]
(TRICYCLAZOLE)

(Xb)
[Structure: diphenyl with S, N, NCF₃ groups]
(FLUOBENZIMINE)

and/or
(K) A urea derivative of the formula (XI)
[Structure: Cl-phenyl-CH₂-N(cyclopentyl)-CO-NH-phenyl]
(PENCYCURON)

and/or (L) A sulphonamide derivative of the formula

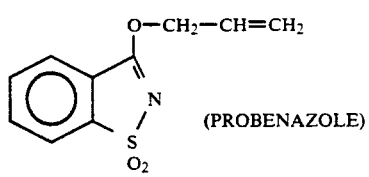
(PROBENAZOLE) (XII)

and/or (M) A polyhydroxy ether derivative of the formula

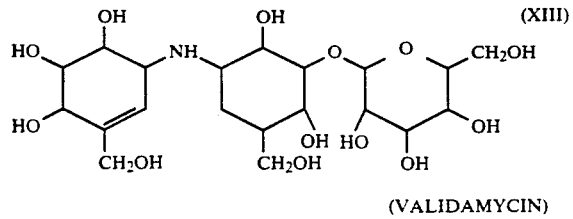
(VALIDAMYCIN) (XIII)

and/or (N) A triazine derivative of the formula

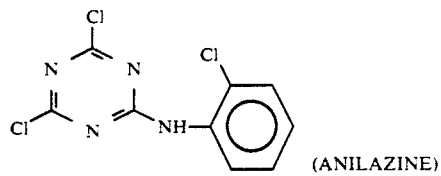
(ANILAZINE) (XIV)

and/or (O) A copper complex salt of the formula

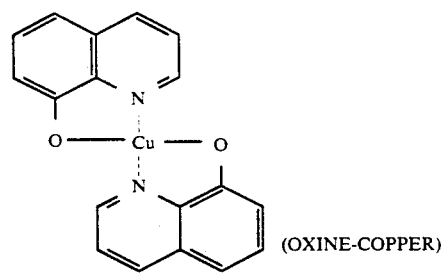
(OXINE-COPPER) (XV)

and/or (P) A N-formyl derivative of the formula

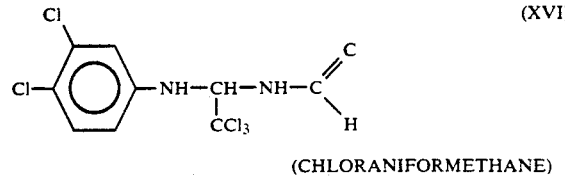
(CHLORANIFORMETHANE) (XVI)

and/or (Q) Morpholine derivatives of the formulae

(TRIDEMORPH) (XVIIa)

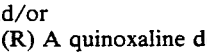
(FENPROPMORPH) (XVIIb)

and/or (R) A quinoxaline derivative of the formula

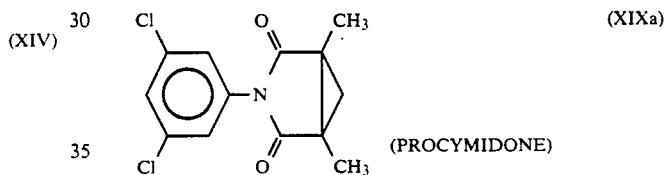
(QUINOMETHIONATE) (XVIII)

and/or (S) A dicarboximide derivative of the formulae

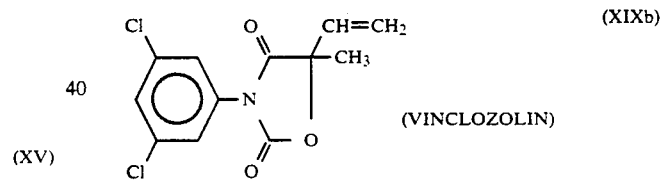
(PROCYMIDONE) (XIXa)

(VINCLOZOLIN) (XIXb)

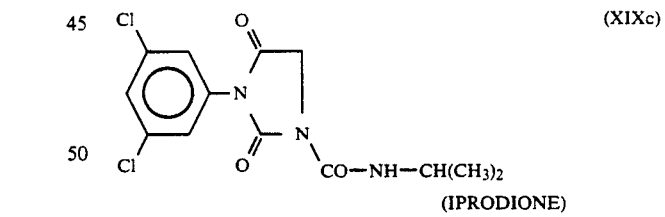
(IPRODIONE) (XIXc)

have a particularly powerful fungicidal activity.

Surprisingly, the fungicidal action of the active compound combinations according to the invention is substantially more powerful than the action of the individual components and, where relevant, also than the sum of the individual components (synergistic effect). The discovery of these combinations of particular compounds of the formula (I) and the active compounds of the abovementioned groups (A), (B), (C), (D), (E), (F), (G), (H), (I), (J), (K), (L), (M), (N), (O), (P), (Q), (R) and (S) thus represents a useful enrichment of the art.

The above formula (I) provides an umabiguous definition of the substituted 1-hydroxyethyl-triazolyl derivatives to be used for the combination according to the invention. If A represents the grouping —CH=CH—, two geometric isomer forms (cis/trans) are possible. The formula (I) includes the following compounds:

(Ia) A = —CH$_2$—CH$_2$—
(Ib) A = —CH=CH— (trans-Form)
(Ic) A = —CH=CH— (cis-Form)

The compounds mentioned and their preparation have already been described (compare EP-OS (European Published Specifications) 0,040,345 and EP-OS (European Published Specification) 0,052,424).

The compounds of the abovementioned groups (A), (B), (C), (D), (E), (F), (G), (H), (I), (J), (K), (L), (M), (N), (O), (P), (Q), (R) and (S) to be used as components of the mixture have already been described in the literature; in this context, compare the following information:

(A): R. Wegler, "Chemie der Pflanzenschutz- und Schädlingsbekämpfungsmittel" ("Chemistry of the Plant Protection Agents and Agents for combating pests"), volume 2, page 51, Springer Verlag Berlin/Heidelberg/New York, 1970;

(B): R. Wegler, loc.cit., pages 95, 108, 109 and 110;

(C): R. Wegler, loc.cit., page 70;

(D): K. H. Büchel, "Pflanzenschutz und Schädlingsbekampfung" (Plant Protection and Combating Pests"), page 146, Georg Thieme Verlag, Stuttgart, 1977;

(E): R. Wegler, loc.cit., pages 65 and 66;

(F): DE-AS (German Published Specification) 1,209,799, DE-OS (German Published Specification) 1,932,297 and U.S. Pat. No. 3,010,968;

(G): See U.S. Pat. No. 3,912,752 issued Oct. 14, 1975 and U.S. Pat. No. 3,952,002 issued Apr. 20, 1976; DE-OS (German Published Specification) 2,063,857, DE-AS (German Published Specification 2,429,523, DE-OS (German Published Specification) 3,018,866, U.S. Ser. No. 458,086 filed Jan. 14, 1983, now abandoned and U.S. Ser. No. 534,233 filed Sep. 21, 1983, now U.S. Pat. No. 4,548,945.

(H): R. Wegler, loc.cit., page 132;

(I): See U.S. Ser. No. 527,442 filed Aug. 29, 1983, now U.S. Pat. No. 4,537,888 and U.S. Pat. No. 3,917,838;

(J): DE-OS (German Published Specification) 2,250,077 and DE-OS (German Published Specification) 2,062,348:

(K): DE-OS (German Published Specification) 2,732,257;

(L): K. H. Büchel, loc.cit., page 142;

(M): Chem. Commun. 1972, No. 12, pages 747–748;

(O): R. Wegler, loc.cit., page 112;

(P): R. Wegler, loc.cit., page 97;

(Q): K. H. Büchel, loc.cit., page 149; DE-OS (German Published Specification 2,656,747;

(R): R. Wegler, loc.cit., page 128 and (S) K. H. Büchel, loc.cit., page 148.

Preferred active compound combinations are those of the substituted 1-hydroxyethyl-triazolyl derivative of the formula (Ia) and an active compound of the formulae (IIa), (IIb), (IIc), or (IId); and/or an active compound of the formula (III); and/or an active compound of the formula (IV); and/or an active compound of the formulae (Va), (Vb), (Vc) or (Vd); and/or an active compound of the formula (VIIe); and/or an active compound of the formula (VIII); and/or and active compound of the formula (Ixa); and/or an active compound of the formula (Ixa); and/or an active compound of the formula (Xa); and/or an active compound of the formula (XI); and/or an active compound of the formula (XII); and/or an active compound of the formula (XIII).

Other active compounds (for example as third components) can also be added to an active compound combination of the substituted 1-hydroxyethyl-triazolyl derivatives of the formula (I) and the active compounds from groups (A) and/or (B) and/or (C) and/or (D) and/or (E) and/or (F) and/or (G) and/or (H) and/or (I) and/or (J) and/or (K) and/or (L) and/or (M) and/or (N) and/or (O) and/or (P) and/or (Q) and/or (R) and/or (S).

The weight ratios of the groups of active compounds in the active compound combination can vary within relatively wide limits. In general, 0.1 to 500 parts by weight of active compound from the active compound classes (A) to (S), preferably 0.2 to 200 parts by weight from the latter and particularly preferably 0.5 to 50 parts by weight, are present per part by weight of compound of the formula (I).

The active compound combinations according to the invention exhibit a powerful microbicidal action and can be employed in practice for combating undesired micro-organisms; they are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compound combinations at the concentrations required for combating plant diseases, permits treatment of above-ground parts of plants, of vegetable propagation stock and seeds, and of the soil.

The active compound combinations according to the invention have a very good action spectrum and can be used against parasitic fungi which infest above-ground parts of plants or attack plants from the soil, as well as seed-born pathogens. Such active compound combinations are of particular practical importance as seed dressing against phytopathogenic fungi which are carried by the seed or occur in the soil and infest the crop plants from there. The diseases are damping off diseases, root rot and diseases of the stem, stalk, leaf, blossom, fruit and seed, which are caused, in particular, by species of Tilletia, Urocystis, Ustilago, Septoria, Typhula, Rhynchosporium, Helminthosporium and Fusarium. As a result of the systemic action of one of the mixing partners, the plants are also frequently still protected for a relatively long time after dressing from pathogens which may attack various parts of the shoot, for example powdery mildew fungi and rust fungi. In addition, the active compound combinations can also be used as soil treatment agents against phytopathogenic fungi and have an action against root rots and trachiomycoses caused, for example, by pathogens of the genera Pythium, Verticillium, Phialophora, Rhizoctonia, Fusarium and Thielaviopsis.

However, when applied directly to the above-ground parts of plants, the active compound combinations according to the invention also show an outstanding action against pathogens on various crop plants, such as powdery mildew fungi (species of Erysiphe, Uncinula, Sphaerotheca and Podosphaera and *Leveillula taurica*), rust fungi, Venturia species, Cercospora species, Alternaria species, Botrytis species, Phytophthora species, Peronospora species, Fusarium species, Pyrenophora species, Cochliobolus species, Septoria species, *Pseudo-*

*cercosporella herpotrichoides, Pyricularia oryzae* and *Pellicularia sasakii.* the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorgainc and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinylacetate, as well as natural phospholids, such as cephalines and lecithins, and synthetic phospholipids can be used in the formulations. Further additions may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention are present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules.

They are used in the customary manner, for example by watering, immersion, spraying, atomizing, misting, vaporizing, injecting, forming a slurry, brushing one, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil active compound concentrations of 0.00001 to 0.1% by weight, preferably 0.0001 to 0.02% by weight, are required at the place of action.

The following use examples serve for illustration.

EXAMPLE A

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

TABLE A

| Sphaerotheca Test (Cucumber)/Protective | | |
|---|---|---|
| Active Compound | Infestation in % at an active compound concentration of | |
| Wettable sulphur (known) | 0.0025 | 100 |
| (VIIa) (known) (TRIADIMEFON) | 0.00005 | 43 |
| (Ia) (known) | 0.00005 | 23 |
| Mixture of (Ia) and wettable sulphur (Mixing ratio 1:50) | 0.00005 +0.0025 | 9 |
| Mixture of (Ia) and (VIIa) (Mixing ration 1:1) | 0.00005 +0.00005 | 6 |

EXAMPLE B

Phytophthora Test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabinet 100% relative atmospheric humidity and at about 20° C.

Evaluation is carried out 3 days after the inoculation.

TABLE B

| Phytophthora Test (Tomato)/Protective | | |
|---|---|---|
| Active Compound | Infestation in % at an active compound concentration of | |
| (IIa) (known) (DICHLOFLUANID) | 0.00025 | 54 |
| (Ia) (known) | 0.000005 | 83 |
| Mixture of (Ia) and (IIa) (Mixing ratio 1:50) | 0.000005 +0.00025 | 37 |

EXAMPLE C

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In order to demonstrate synergism between the active compounds used in this experiment, the results were evaluated according to the method described by R. S. Colby (Calculating Synergistic and Antagonistic Responses of Herbicides Combinations; Weeds 15, 20–22, 1967). The expected infestation in percent of the untreated control was calculated from the equation $$E = \frac{X \cdot Y}{100}$$

In this equation, X and Y denote the disease infestation —expressed in percent of the untreated control—attributed to the two products when these are used separately. A synergistic effect exists if the fungicidal action of the active compounds combination is greater than that of the active compound used individually. In this case, the actual infestation observed must be smaller than the value calculated for the expected infestation (E) from the above formula.

TABLE C

| Leptosphaeria nodorum Test (Wheat)/Protective | | | |
|---|---|---|---|
| Active Compound | | Active compound concentration in the spray liquor in % by weight | Disease infestation in % of the untreated control |
| | (Ia) (known) | 0.025 | 100 |
| CAPTAFOL | (IId) (known) | 0.01 | 82.5 |
| ANILAZIN | (XIV) (known) | 0.005 | 64.8 |
| | | observed Infestation after use of the mixture in % of the untreated control | expected Infestation (E) after use of the mixture |
| Mixture of Ia and IId (Mixing ratio 2.5:1) | | 0.025 +0.01 | 50.0 | 82.5 |
| Mixture of Ia and XIV (Mixing ratio 5:1) | | 0.025 +0.005 | 50.0 | 64.8 |

PREPARATION EXAMPLES

EXAMPLE 1A

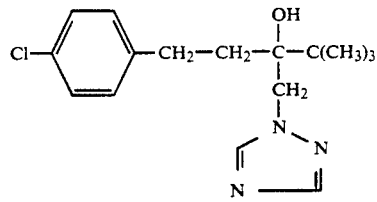

A solution of 17.9 g (0.075 mol) of 2-(4-chlorophenylethyl)-2-tert.-butyl-oxirane and 6.9 g (0.1 mol) of 1,2,4-triazole in 30 ml of ethanol is heated at 150° C. in a bomb tube for 20 hours. The reaction solution is allowed to cool and is concentrated. The residue is dissolved in ether and the solution is washed three times with water and once with sodium chloride solution, dried over sodium sulphate and concentrated. The residue is chromatographed over a silica gel column (running agent: methylene chloride/ethyl acetate=1:1).

12.3 g (53.2% of theory) of 1-(4-chlorophenyl)-4,4-dimethyl-3-(1,2,4-triazol-1-yl-methyl) -pentan-3-ol obtained as a viscous oil, which can be recrystallized from acetonitrile (melting point 102° C. to 104° C.).

EXAMPLE 1B

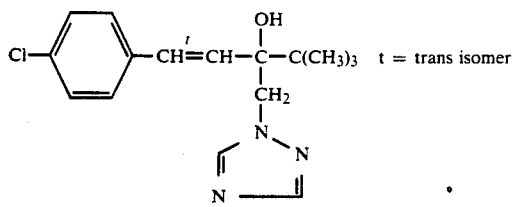

13.8 g (0.2 mol) of 1,2,4-triazole are slowly added to a suspension of 6 g (0.2 mol) of sodium hydride (80% strength in paraffin oil) in 200 ml of absolute dimethylformamide. When the reaction has subsided, a solution of 23.7 g (0.1 mol) of 2-(trans-4-chlorophenylethenyl)-2-tert.-butyl oxirane in 50 ml of absolute dimethylformamide is added dropwise. The reaction mixture is then stirred at 80° C. for 4 hours and subsequently cooled and poured onto 1 liter of ice/water. The mixture is stirred overnight and the solid is filtered off with suction. This is washed with water and taken up in ethyl acetate and the mixture is washed again twice with water and then once with sodium chloride solution, dried over sodium sulphate and concentrated. The crystalline residue is purified over a silica gel column (running agent: methylene chloride/ethyl acetate=1:1) and recrystallized from ligroin.

11.5 g of trans-1-(4-chlorophenyl)-4,4-dimethyl-3-(1,2,4-triazol-1-yl-methyl)-1-penten -3ol of melting point 115° C. to 117° C. are obtained.

EXAMPLE 1C

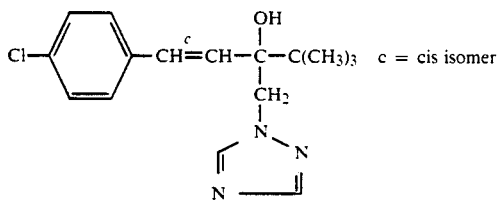

15.0 g of 1-(4-chlorophenyl)-4,4-dimethyl-3-(1,2,4-triazol-1-yl-methyl)-1-penten-3-ol are dissolved in 175 ml of methanol and the solution is exposed to a high pressure mercury lamp, as an immersion lamp. The radiation is filtered through a Duran tube 1.2 mm thick, so that only light of wavelength greater than 280 nm reaches the sample. After an exposure time of 28 hours, analysis by HPLC showed 95% conversion to the cis isomer. The solvent is distilled off and the crystalline residue is purified by thick layer chromatography (silica gel; chloroform/ethanol=98.2).

14.7 g of cis-1-(4-chlorophenyl)-4,4-dimethyl-3-(1,2,4-triazol-1-yl-methyl)-1-penten-3-ol of melting point 81° C. to 83.5° C. are obtained.

It is understood that the specification and examples are illustrative but not limitative of the present invention and that other embodiments within the spirit and scope of the invention will suggest themselves to those skilled in the art.

We claim:

1. A fungicidal composition comprising a synergistic fungicidally effective amount of the mixture of

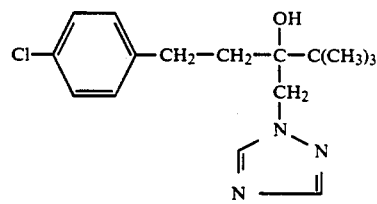

and a synergistically approximately equal amount by weight of a dicarboximide derivative of the formula

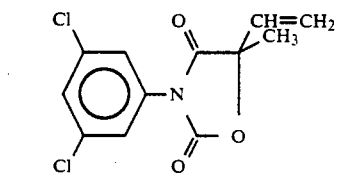

or

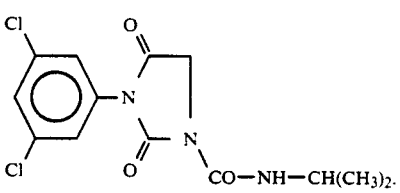

2. A method of combating fungi which comprises administering to such fungi or to a fungus habitat a fungicidally effective amount of a composition according to claim 1.

* * * * *